US008529671B2

(12) United States Patent
Sebastian et al.

(10) Patent No.: US 8,529,671 B2
(45) Date of Patent: Sep. 10, 2013

(54) ELECTRET WEBS WITH CHARGE-ENHANCING ADDITIVES

(75) Inventors: John M. Sebastian, Oakdale, MN (US); Fuming B. Li, Woodbury, MN (US); Marvin E. Jones, Grant, MN (US); Luke T. Dressel, Somerset, WI (US); Daniel A. Japuntich, St. Paul, MN (US)

(73) Assignee: 3M Innovative Properties Comany, St. Paul, MN (US)

( * ) Notice: Subject to any disclaimer, the term of this patent is extended or adjusted under 35 U.S.C. 154(b) by 508 days.

(21) Appl. No.: 12/746,112

(22) PCT Filed: Nov. 25, 2008

(86) PCT No.: PCT/US2008/084686
§ 371 (c)(1),
(2), (4) Date: Oct. 19, 2010

(87) PCT Pub. No.: WO2009/076064
PCT Pub. Date: Jun. 18, 2009

(65) Prior Publication Data
US 2011/0041471 A1    Feb. 24, 2011

Related U.S. Application Data

(60) Provisional application No. 60/992,745, filed on Dec. 6, 2007.

(51) Int. Cl.
*B01D 46/00* (2006.01)
(52) U.S. Cl.
USPC ................. 96/66; 442/110; 442/115; 55/524; 55/528; 55/DIG. 5; 55/DIG. 39
(58) Field of Classification Search
USPC .............. 442/110–116; 55/522–528, DIG. 5; 264/121, 446–448; 95/273–287
See application file for complete search history.

(56) References Cited

U.S. PATENT DOCUMENTS

| | | |
|---|---|---|
| 2,204,705 A | 6/1940 | Scofield |
| 3,070,573 A | 12/1962 | Beck |
| 3,309,222 A | 3/1967 | Caldwell |
| 3,971,373 A | 7/1976 | Braun |
| 3,988,157 A | 10/1976 | Van Paesschen |
| 3,998,916 A | 12/1976 | van Turnhout |
| 4,016,375 A | 4/1977 | Van Turnhout |
| 4,029,582 A | 6/1977 | Ishii |
| 4,049,870 A | 9/1977 | Brodmann |
| 4,100,324 A | 7/1978 | Anderson |
| 4,118,531 A | 10/1978 | Hauser |
| 4,178,157 A | 12/1979 | van Turnhout |
| 4,215,682 A | 8/1980 | Kubik |
| 4,238,193 A | 12/1980 | Kisaichi |
| 4,264,750 A | 4/1981 | Anand |
| RE30,782 E | 10/1981 | van Turnhout |
| 4,375,718 A | 3/1983 | Wadsworth |
| RE31,285 E | 6/1983 | van Turnhout |
| 4,429,001 A | 1/1984 | Kolpin |
| 4,508,781 A | 4/1985 | Yagi |
| 4,523,995 A | 6/1985 | Pall |
| 4,536,440 A | 8/1985 | Berg |
| 4,547,420 A | 10/1985 | Krueger |
| 4,557,945 A | 12/1985 | Yagi |
| 4,588,537 A | 5/1986 | Klaase |
| RE32,171 E | 6/1986 | van Turnhout |
| 4,592,815 A | 6/1986 | Nakao |
| 4,617,124 A | 10/1986 | Pall |
| 4,617,390 A | 10/1986 | Hoppe |
| 4,652,282 A | 3/1987 | Ohmori |
| 4,729,371 A | 3/1988 | Krueger |
| 4,789,504 A | 12/1988 | Ohmori |
| 4,795,668 A | 1/1989 | Krueger |
| 4,798,850 A | 1/1989 | Brown |
| 4,807,619 A | 2/1989 | Dyrud |
| 4,827,924 A | 5/1989 | Japuntich |
| 4,850,347 A | 7/1989 | Skov |
| 4,883,547 A | 11/1989 | Japuntich |
| 5,025,052 A | 6/1991 | Crater |
| 5,057,710 A | 10/1991 | Nishiura |
| 5,062,421 A | 11/1991 | Burns |
| 5,099,026 A | 3/1992 | Crater |
| 5,237,986 A | 8/1993 | Seppala |
| 5,280,406 A | 1/1994 | Coufal |

(Continued)

FOREIGN PATENT DOCUMENTS

| | | |
|---|---|---|
| EP | 623941 | 11/1994 |
| JP | 55-053410 | 4/1980 |

(Continued)

OTHER PUBLICATIONS

Buu-Hoi, The Scope of the Knoevenagel Synthesis of Aromatic Secondary Amines, Journal of the Chemical Society, pp. 4346-4349, (1952).
Chudleigh, Charging of Polymer Foils Using Liquid Contacts, Appl. Phys. Lett., vol. 21, No. 11, pp. 547-548, (Dec. 1, 1972).
Chudleigh, Mechanism of Charge Transfer to a Polymer Surface by a Conducting Liquid Contact, Journal of Applied Physics, vol. 47, No. 10, pp. 4475-4483, (Oct. 1976).
Davies, "The Separation of Airborne Dust and Particles", Institute of Mechanical Engineers, London, Proceedings 1B, pp. 185-213, (1952).
Dean, Physicochemical Relationships, Lange's Handbook of Chemistry, Section 9, 15th Edition, McGraw-Hill, New York, pp. 9.1-9.8, (1999).

(Continued)

*Primary Examiner* — Duane Smith
*Assistant Examiner* — Thomas McKenzie
(74) *Attorney, Agent, or Firm* — Jeffrey M. Olotson

(57) ABSTRACT

Electret webs are presented which include a blend of a thermoplastic resin and a charge additive. The charge additives include ester-substituted and amide-substituted trianilino triazine materials. The webs prepared from the blends may be in the form of films or non-woven fibrous webs. Non-woven microfiber webs are useful as filtration media.

20 Claims, No Drawings

(56) References Cited

U.S. PATENT DOCUMENTS

| | | |
|---|---|---|
| 5,307,796 A | 5/1994 | Kronzer |
| 5,325,892 A | 7/1994 | Japuntich |
| 5,346,691 A | 9/1994 | Raspanti |
| 5,374,458 A | 12/1994 | Burgio |
| 5,401,446 A | 3/1995 | Tsai |
| 5,411,576 A | 5/1995 | Jones |
| RE35,062 E | 10/1995 | Brostrom |
| 5,464,010 A | 11/1995 | Byram |
| 5,472,481 A | 12/1995 | Jones |
| 5,496,507 A | 3/1996 | Angadjivand |
| 5,502,118 A | 3/1996 | Macholdt |
| 5,509,436 A | 4/1996 | Japuntich |
| 5,543,054 A | 8/1996 | Charkoudian |
| 5,558,089 A | 9/1996 | Castiglione |
| 5,656,368 A | 8/1997 | Braun |
| 5,696,199 A | 12/1997 | Senkus |
| 5,763,078 A | 6/1998 | Braun |
| 5,780,153 A | 7/1998 | Chou |
| 5,804,295 A | 9/1998 | Braun |
| 5,908,598 A | 6/1999 | Rousseau |
| 5,919,847 A | 7/1999 | Rousseau |
| D412,573 S | 8/1999 | Castiglione |
| 5,968,635 A | 10/1999 | Rousseau |
| 5,976,208 A | 11/1999 | Rousseau |
| 6,041,782 A | 3/2000 | Angadjivand |
| 6,068,799 A | 5/2000 | Rousseau |
| 6,072,027 A | 6/2000 | Scortichini |
| 6,074,869 A | 6/2000 | Pall |
| 6,095,143 A | 8/2000 | Dyrud |
| 6,119,691 A | 9/2000 | Angadjivand |
| 6,156,086 A | 12/2000 | Zhang |
| 6,174,964 B1 | 1/2001 | Jariwala |
| 6,187,391 B1 | 2/2001 | Kataoka |
| 6,213,122 B1 | 4/2001 | Rousseau |
| 6,214,094 B1 | 4/2001 | Rousseau |
| 6,216,693 B1 | 4/2001 | Rekow |
| 6,238,466 B1 | 5/2001 | Rousseau |
| 6,268,495 B1 | 7/2001 | Rousseau |
| 6,280,824 B1 | 8/2001 | Insley |
| 6,302,103 B1 | 10/2001 | Resnick |
| 6,332,465 B1 | 12/2001 | Xue |
| 6,371,116 B1 | 4/2002 | Resnick |
| 6,375,886 B1 | 4/2002 | Angadjivand |
| 6,391,948 B1 | 5/2002 | Clark |
| 6,394,090 B1 | 5/2002 | Chen |
| 6,397,458 B1 | 6/2002 | Jones |
| 6,398,847 B1 | 6/2002 | Jones |
| 6,406,657 B1 | 6/2002 | Eitzman |
| 6,409,806 B1 | 6/2002 | Jones |
| 6,419,871 B1 | 7/2002 | Ogale |
| 6,432,175 B1 | 8/2002 | Jones |
| 6,454,986 B1 | 9/2002 | Eitzman |
| 6,484,722 B2 | 11/2002 | Bostock |
| RE37,974 E | 2/2003 | Bowers |
| 6,562,112 B2 | 5/2003 | Jones |
| 6,575,165 B1 | 6/2003 | Cook |
| D480,476 S | 10/2003 | Martinson |
| 6,660,210 B2 | 12/2003 | Jones |
| 6,666,209 B2 | 12/2003 | Bennett |
| 6,673,447 B2 | 1/2004 | Wei |
| 6,701,925 B1 | 3/2004 | Resnick |
| 6,743,464 B1 | 6/2004 | Insley |
| 6,752,889 B2 | 6/2004 | Insley |
| 6,776,951 B2 | 8/2004 | Rousseau |
| 6,780,893 B2 | 8/2004 | Sugaya |
| 6,783,574 B1 | 8/2004 | Angadjivand |
| 6,808,551 B2 | 10/2004 | Jones |
| 6,824,718 B2 | 11/2004 | Eitzman |
| 6,843,248 B2 | 1/2005 | Japuntich |
| 6,854,463 B2 | 2/2005 | Japuntich |
| 6,872,645 B2 | 3/2005 | Duan |
| 6,969,484 B2 | 11/2005 | Horiguchi |
| 7,013,895 B2 | 3/2006 | Martin |
| 7,015,254 B2 | 3/2006 | Holcomb |
| 7,026,014 B2 | 4/2006 | Luzinov |
| 7,028,689 B2 | 4/2006 | Martin |
| 7,117,868 B1 | 10/2006 | Japuntich |
| 7,132,496 B2 | 11/2006 | Kerres |
| 7,188,622 B2 | 3/2007 | Martin |
| 7,244,291 B2 | 7/2007 | Spartz |
| 7,244,292 B2 | 7/2007 | Kirk |
| 7,311,104 B2 | 12/2007 | Japuntich |
| 7,390,351 B2 | 6/2008 | Leir |
| 7,441,666 B2 | 10/2008 | Kim |
| 7,462,283 B2 | 12/2008 | Kelly |
| 7,765,698 B2 | 8/2010 | Sebastian |
| 2002/0174869 A1 | 11/2002 | Gahan |
| 2003/0134515 A1 | 7/2003 | David |
| 2004/0067427 A1 | 4/2004 | Tong |
| 2004/0116028 A1* | 6/2004 | Bryner .................. 442/381 |
| 2005/0176325 A1 | 8/2005 | Tokuda |
| 2006/0093820 A1 | 5/2006 | Margarit-Puri |
| 2006/0096486 A1 | 5/2006 | Roller |
| 2006/0254419 A1 | 11/2006 | Leonard |
| 2007/0134337 A1 | 6/2007 | Villanueva |
| 2007/0141130 A1 | 6/2007 | Villanueva |
| 2007/0142262 A1 | 6/2007 | Sayre |
| 2007/0180997 A1 | 8/2007 | Leir |
| 2008/0207822 A1 | 8/2008 | Yeager |
| 2008/0249269 A1 | 10/2008 | Chin |
| 2010/0112886 A1* | 5/2010 | Chin et al. .................. 442/327 |
| 2011/0137082 A1 | 6/2011 | Li |
| 2011/0154987 A1 | 6/2011 | Li |

FOREIGN PATENT DOCUMENTS

| | | |
|---|---|---|
| JP | 06-218211 | 8/1994 |
| JP | 11-319441 | 11/1999 |
| JP | 2002-115177 | 4/2002 |
| JP | 2002-115178 | 4/2002 |
| JP | 2002-161467 | 6/2002 |
| JP | 2002-161471 | 6/2002 |
| JP | 2002-173866 | 6/2002 |
| JP | 2002-212439 | 7/2002 |
| JP | 2002-249978 | 9/2002 |
| JP | 2002-339232 | 11/2002 |
| JP | 2003-013359 | 1/2003 |
| JP | 2003-220310 | 8/2003 |
| JP | 2004-060110 | 2/2004 |
| JP | 2004-066026 | 3/2004 |
| JP | 2004-066027 | 3/2004 |
| JP | 2004-195357 | 7/2004 |
| JP | 2005-131484 | 5/2005 |
| JP | 2005-131485 | 5/2005 |
| JP | 2006-037295 | 2/2006 |
| JP | 3780916 | 5/2006 |
| JP | 2008-081894 | 4/2008 |
| JP | 2009-079092 | 4/2009 |
| RU | 2198718 | 2/2003 |
| WO | WO 95-05501 | 2/1995 |
| WO | WO 97-07272 | 2/1997 |
| WO | WO 99-16532 | 4/1999 |
| WO | WO 99-16533 | 4/1999 |
| WO | WO 00-13765 | 3/2000 |
| WO | WO 01-07144 | 2/2001 |
| WO | WO 01-23351 | 4/2001 |
| WO | WO 01-27371 | 4/2001 |
| WO | WO 01-27381 | 4/2001 |
| WO | WO 03-023796 | 3/2003 |
| WO | WO 2006-096486 | 9/2006 |
| WO | WO 2008-016782 | 2/2008 |

OTHER PUBLICATIONS

Delgado, Measurement and Interpretation of Electrokinetic Phenomena (IUPAC Technical Report), Pure and Applied Chemistry, vol. 77, No. 10, pp. 1753-1805, (2005).

Easton, The MIDI! Basis Set for Quantum Mechanaical Calculations of Molecular Geometries and Partial Charges, Theoretica Chimica Acta, vol. 93, pp. 281-301, (1996).

Fairbrother, Studies in Electro-Endosmosis, Part I., vol. 125, J. Chem. Soc., pp. 2319-2330, (1924).

Foresman, Exploring Chemistry With Electronic Structure Methods, 2nd Ed., 7 pages, (1996).

Gal, Thermochemical Aspects of Proton Transfer in the Gas Phase, Journal of Mass Spectrometry, vol. 36, pp. 699-716, (2001).

Harist, Back to Basics Measuring PH in High-Purity Water, Ultrapure Water, pp. 75-76, (Oct. 1994).

Hehre, Ab Initio Molecular Orbital Theory, Wiley, New York, 10 pages, (1986).

Kohn, Nobel Lecture: Electronic Structure of Matter—Wave Functions and Density Functionals, Reviews of Modern Physics, vol. 71, No. 5, pp. 1253-1266, (Oct. 1999).

Kohn, Self-Consistent Equations Including Exchange and Correlation Effects, Physical Review, vol. 140, No. 4A, p. A1133-A1138, (Nov. 15, 1965).

Kudin, Why Are Water-Hydrophobic Interfaces Charged?, Journal of American Chemical Society, pp. A-E, (2007).

Lias, Gas Phase Ion Thermochemistry, NIST Chemistry WebBook, NIST Standard Reference Database No. 69, National Institute of Standards and Technology, Gaithersburg, MD, (http://webbook.nist.gov), pp. 1-38, (Jun. 2005).

McCarty, Electrostatic Charging Due to Separation of Ions at Interfaces: Contact Electrification of Ionic Electrets, Angewandte Chemie Int. Ed., vol. 47, pp. 2-22, (2008).

McCarty, Ionic Electrets: Electrostatic Charging of Surfaces by Transferring Mobile Ions Upon Contact, Journal American Chemical Society, vol. 129, pp. 4075-4088, (2007).

Shishkin, Structural Non-Rigidity of Six-Membered Aromatic Rings, Journal of Molecular Structure, vol. 616, pp. 159-166, (2002).

Stephens, Ab Initio Calculation of Vibrational Absorption and Circular Dichroism Spectra Using Density Functional Force Fields, Journal of Phys. Chemistry, vol. 98, No. 45, pp. 11623-11627 (Nov. 10, 1994).

Vargas, "An Overview of Raw Materials, Processes, Products, Markets, and Emerging End Uses", Spunlace Technology Today, Miller Freeman Publications, Inc., 1989, pp. 9-12, 132-133, 142-146.

Wente, "Manufacture of Superfine Organic Fibers", Report No. 4364 of the Naval Research Laboratories, 22 pages, (May 25, 1954).

Wente, "Manufacture of Superfine Organic Fibers", Naval Research Laboratory Report 111437, pp. ii-15, (Apr. 15, 1954).

Wente, "Superfine Thermoplastic Fibers", Industrial Engineering Chemistry, vol. 48, pp. 1342-1346, (1956).

Zhao, Design of Density Functionals That Are Broadly Accurate for Thermochemistry, Thermochemical Kinetics, and Nonbounded Interactioins, Journal Phys. Chem. A, vol. 109, No. 25, pp. 5656-5667, (2005).

Search Report for PCT/US2008/084686, 3 pages.
Search Report for PCT/US2009/042652, 3 pages.
Search Report for PCT/US2009/040426, 4 pages.
Search Report for PCT/US2009/042689, 3 pages.

* cited by examiner

ELECTRET WEBS WITH CHARGE-ENHANCING ADDITIVES

CROSS REFERENCE TO RELATED APPLICATIONS

This application is a national stage filing under 35 U.S.C. 371 of PCT/US2008/084686, filed Nov. 25, 2008, which claims priority to U.S. Application No. 60/992,745, filed Dec. 6, 2007, the disclosure of which is incorporated by reference in its/their entirety herein.

FIELD OF THE DISCLOSURE

This disclosure relates to electret webs, including non-woven fibrous webs such as non-woven thermoplastic microfiber webs, containing charge-enhancing additives and uses thereof.

BACKGROUND

An electret is a dielectric material exhibiting a quasi-permanent electrical charge. Electrets are useful in a variety of devices including, e.g. cling films, air filters, filtering facepieces, and respirators, and as electrostatic elements in electro-acoustic devices such as microphones, headphones, and electrostatic recorders.

The performance of microfibrous webs used for aerosol filtration can be improved by imparting an electrical charge to the fibers, forming an electret material. In particular, electrets are effective in enhancing particle capture in aerosol filters. A number of methods are known for forming electret materials in microfibrous webs. Such methods include, for example, bombarding melt-blown fibers as they issue from the die orifices, as the fibers are formed, with electrically charged particles such as electrons or ions. Other methods include, for example, charging the fibers after the web is formed, by means of a DC corona discharge or imparting a charge to the fiber mat by means of carding and/or needle tacking (tribocharging). Recently, a method in which jets of water or a stream of water droplets impinge on a non-woven web at a pressure sufficient to provide filtration enhancing electret charge has been described (hydrocharging).

SUMMARY

The need remains for electret webs with improved properties. Presented in this disclosure are electret webs containing charge-enhancing additives. These charge enhancing additives provide electret webs that are easy to charge by a variety of different charging mechanisms such as DC corona discharge, hydrocharging or a combination thereof. In addition, the electret webs containing charge-enhancing additives have relatively long charge retention capability.

In some embodiments the disclosure includes an electret web comprising a thermoplastic resin and a charge additive comprising an ester-substituted and/or amide-substituted trianilino triazine material. The electret web may be in the form of a non-woven fibrous web or even a non-woven microfiber web.

In other embodiments the disclosure includes an electret filter media comprising a non-woven microfiber web comprising a blend of a thermoplastic resin and a charge additive comprising an ester-substituted and/or amide-substituted trianilino triazine material. The electret filter media may comprise a respirator filter, a room ventilation system filter, a vehicle ventilation system filter, an air conditioner filter, a furnace filter, a room air purifier filter, a vacuum cleaner filter, or a computer disk drive filter.

Also disclosed are methods for preparing an electret web comprising providing a thermoplastic material, providing a hot melt processable charge additive comprising an ester-substituted and/or amide-substituted trianilino triazine material, hot melt mixing the thermoplastic material and the charge additive, and melt blowing the mixed thermoplastic material and charge additive to form a microfiber web, and charging the web.

DETAILED DESCRIPTION

Electret webs useful in the present disclosure include a blend of a thermoplastic resin and a charge additive. Webs prepared from such blends show enhanced properties over webs prepared with the thermoplastic resins alone. Useful charge additives include ester-substituted and amide-substituted trianilino triazine materials.

The electret webs may be in a variety of forms. For example the web may be a continuous or discontinuous film, or a fibrous web. Fibrous webs are particularly useful for the formation of filtration media. In some embodiments the web is a non-woven microfibrous web. Typically microfibers are 1-100 micrometers in diameter.

The terms "a", "an", and "the" are used interchangeably with "at least one" to mean one or more of the elements being described.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl (t-butyl), n-pentyl, n-hexyl, cyclohexyl, n-heptyl, n-octyl, and ethylhexyl.

The term "heteroalkyl" refers to an alkyl group which contains heteroatoms. These heteroatoms may be halogens such as fluorine, chlorine, bromine, or iodine or other atoms such as nitrogen, oxygen or sulfur. An example of a heteroalkyl group is a polyoxyalkyl group such as —$CH_2CH_2$(O$CH_2CH_2$)$_n$O$CH_2CH_2$—.

The term "substituted alkyl" refers to an alkyl group which contains substituents along the hydrocarbon backbone. These substituents may be alkyl groups, heteroalkyl groups or aryl groups. An example of a substituted alkyl group is a benzyl group.

The term "aryl" refers to an aromatic carbocyclic group that is a radical containing 1 to 5 rings which may be connected or fused. The aryl group may be substituted with alkyl or heteroalkyl groups. An example of an aryl group is a phenyl group.

The term "substituted trianilino triazine" refers to a material in which 3 substituted aniline rings are attached to a triazine ring as shown in Formula I in which $R^1$, $R^2$ and $R^3$ are the substituents on the trianilino triazine material. When the terms "ester-substituted" and "amide-substituted" are used in conjunction with "substituted trianilino triazine", this means that the groups $R^1$, $R^2$ and $R^3$ are each independently linked to the aniline ring via an ester (—C(O)—O—) or amide (—C(O)NR—) linkage where R in this case is a hydrogen atom or an alkyl group:

Formula I

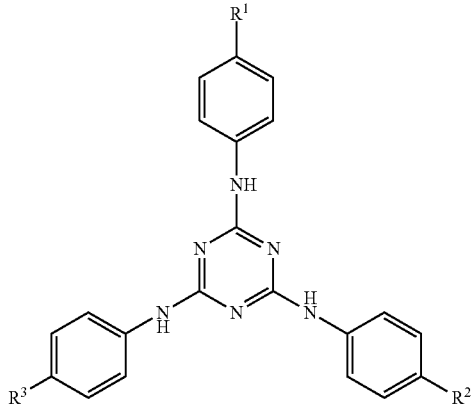

Formula II

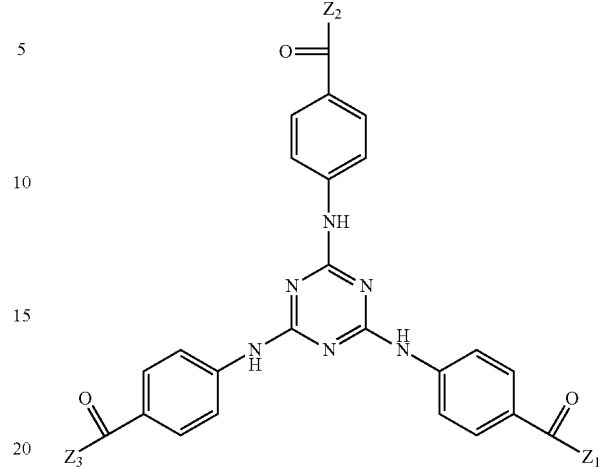

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The terms "room temperature" and "ambient temperature" are used interchangeably to mean temperatures in the range of 20° C. to 25° C.

The term "hot melt processable" as used herein, refers to a composition that can transform, for example, by heat and pressure from a solid to a viscous fluid. The composition should be capable of being hot melt processed without being chemically transformed, degraded or rendered unusable for the intended application.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

Thermoplastic resins useful in the present invention include any thermoplastic nonconductive polymer capable of having a high quantity of trapped electrostatic charge when formed into a web and charged. Typically, such resins have a DC (direct current) resistivity of greater than $10^{14}$ ohm-cm at the temperature of intended use. Polymers capable of acquiring a trapped charge include polyolefins such as polypropylene, polyethylene, and poly-4-methyl-1-pentene; polyvinyl chloride; polystyrene; polycarbonates; and polyesters. Particularly useful materials include polypropylene, poly-4-methyl-1-pentene, blends thereof or copolymers formed from at least one of propylene and 4-methyl-1-pentene.

The charge additives are ester-substituted and/or amide-substituted trianilino triazine materials. It has been observed that materials with ester and/or amide substituents on the aniline rings provide superior electret charge retention over substituents which are, for example, simple alkyl groups. Typically the charge additives are hot melt processable materials. Particularly suitable charge additives include materials described by formula II.

where each $Z_1$, $Z_2$ and $Z_3$ is independently —$OR^4$ (ester-substituted) or —$NR^5R^6$ (amide-substituted) and where each $R^4$ is independently an alkyl group, a substituted alkyl group, a heteroalkyl group, or an aryl group; each $R^5$ is independently H or an alkyl group, a substituted alkyl group, a heteroalkyl group, or an aryl group; each $R^6$ is independently an alkyl group, a substituted alkyl group, a heteroalkyl group, or an aryl group. In some embodiments each $Z_1$, $Z_2$ and $Z_3$ is independently —$OR^4$ where each $R^4$ is independently a linear or branched alkyl group containing from 1 to 20 carbon atoms. In other embodiments, each $Z_1$ and $Z_2$ is independently —$OR^4$ where each $R^4$ is independently a linear or branched alkyl group containing from 1 to 20 carbon atoms and $Z_3$ is —$NR^5R^6$ where $R^5$ is H or a linear or branched alkyl group containing from 1 to 20 carbon atoms and $R^6$ is a linear or branched alkyl group containing from 1 to 20 carbon atoms.

Examples of suitable charge additives include, for example, 2,4,6-trianilino-p-(carbo-2'-ethylhexyl-1'-oxy)-1,3,5-triazine, commercially available from BASF, Ludwigshafen, Germany as UVINUL T-150 shown as Formula III below (Et is an ethyl group, Bu-n is an n-butyl group, and Bu-t is a tert-butyl group); 4,4'-[[6-[[4-[[(1,1-dimethylethyl)amino]carbonyl]phenyl]amino]-1,3,5-triazine-2,4-diyl]diimino]bis-benzoic acid bis(2-ethylhexyl) ester commercially available from 3V Bergamo, Italy as UVASORB HEB shown as Formula IV below; 2,4,6-trianilino(p-carbo-tetradecyl-oxy)-1,3,5-triazine shown as Formula V below; 2,4,6-trianilino(p-carbo-octadecyl-oxy)-1,3,5-triazine shown as Formula VI below; and mixtures thereof.

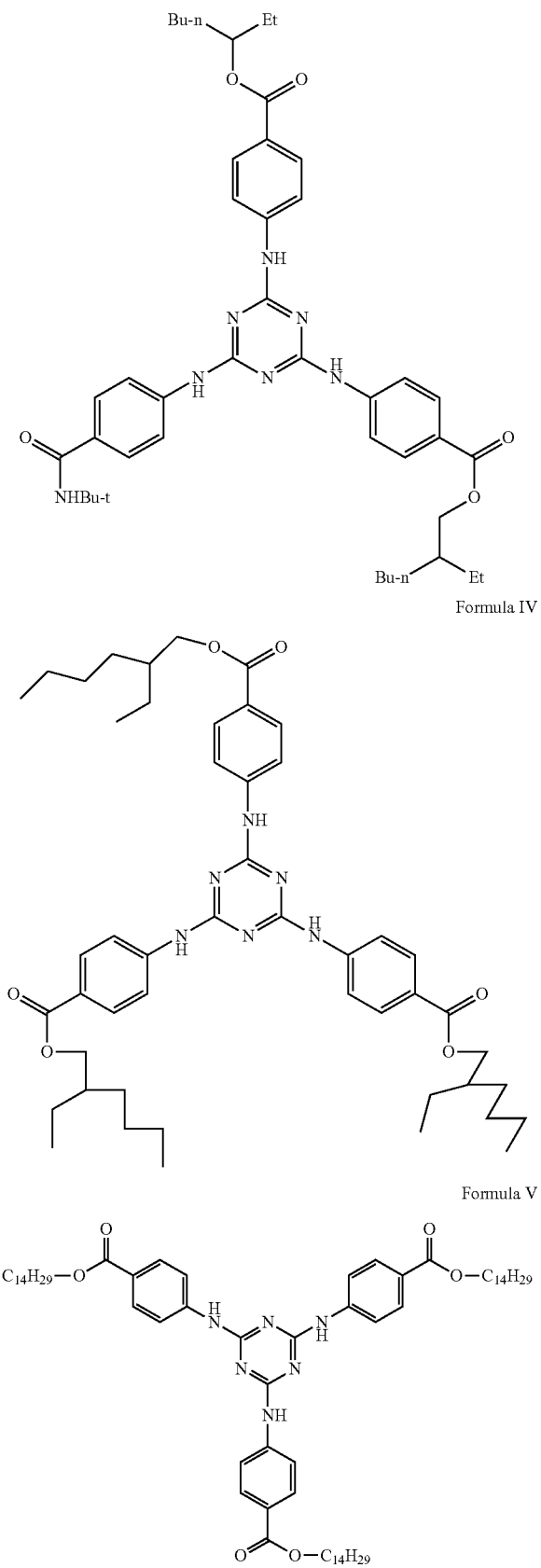

Formula III

Formula IV

Formula V

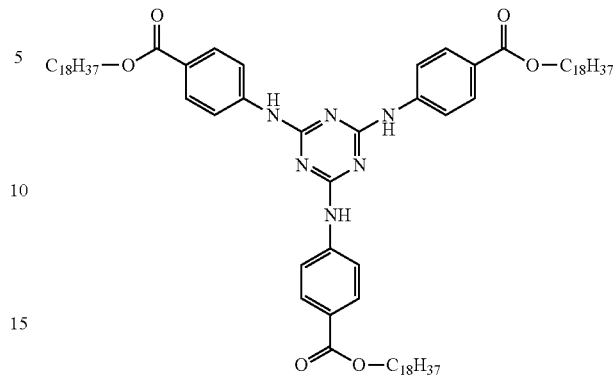

Formula VI

Typically the charge additive is present in the thermoplastic resin/charge additive blend in amounts in the range of 0.1 to 5% by weight based upon the total weight of the blend. In some embodiments the charge additive is present in amounts ranging from 0.1 to 3% by weight or 0.25 to 2% by weight.

The blend of the thermoplastic resin and the charge additive can be prepared by well-known methods. Typically the blend is processed using melt extrusion techniques, so the blend may be preblended to form pellets in a batch process, or the thermoplastic resin and the charge additive may be mixed in the extruder in a continuous process. Where a continuous process is used the thermoplastic resin and the charge additive may be pre-mixed as solids or added separately to the extruder and allowed to mix in the molten state.

Examples of melt mixers that may be used to form preblended pellets include those that provide dispersive mixing, distributive mixing, or a combination of dispersive and distributive mixing. Examples of batch methods include those using a BRABENDER (e.g. a BRABENDER PREP CENTER, commercially available from C.W. Brabender Instruments, Inc.; South Hackensack, N.J.) or BANBURY internal mixing and roll milling equipment (e.g. equipment available from Farrel Co.; Ansonia, Conn.). After batch mixing, the mixture created may be immediately quenched and stored below the melting temperature of the mixture for later processing.

Examples of continuous methods include single screw extruding, twin screw extruding, disk extruding, reciprocating single screw extruding, and pin barrel single screw extruding. The continuous methods can include utilizing both distributive elements, such as cavity transfer mixers (e.g. CTM, commercially available from RAPRA Technology, Ltd.; Shrewsbury, England) and pin mixing elements, static mixing elements or dispersive mixing elements (commercially available from e.g., MADDOCK mixing elements or SAXTON mixing elements).

Examples of extruders that may be used to extrude preblended pellets prepared by a batch process include the same types of equipment described above for continuous processing. Useful extrusion conditions are generally those which are suitable for extruding the resin without the additive.

The extruded blend of thermoplastic resin and charge additive may be cast or coated into films or sheets or may be melt blown into non-woven fibrous webs using known techniques. Melt blown non-woven microfibrous webs are particularly useful as filtration media.

Melt blown non-woven microfibrous electret filters are especially useful as an air filter element of a respirator, such as a filtering facepiece, or for such purposes as home and industrial air-conditioners, air cleaners, vacuum cleaners, medical air line filters, and air conditioning systems for vehicles and common equipment, such as computers, computer disk drives and electronic equipment. In respirator uses, the electret filters may be in the form of molded or folded half-face respirators, replaceable cartridges or canisters, or prefilters.

Melt blown microfibers useful in the present disclosure can be prepared as described in Van A. Wente, "Superfine Thermoplastic Fibers," Industrial Engineering Chemistry, vol. 48, pp. 1342-1346 and in Report No. 4364 of the Naval Research Laboratories, published May 25, 1954, entitled "Manufacture of Super Fine Organic Fibers" by Van A. Wente et al.

Useful melt blown microfibers for fibrous electret filters typically have an effective fiber diameter of from about 3 to 30 micrometers, in some embodiments from about 7 to 15 micrometers, as calculated according to the method set forth in Davies, C. N., "The Separation of Airborne Dust and Particles," Institution of Mechanical Engineers, London, Proceedings 1B, 1952.

Staple fibers may also be present in the web. The presence of staple fibers generally provides a more lofty, less dense web than a web of only blown microfibers. Preferably, no more than about 90 weight percent staple fibers are present, more preferably no more than about 70 weight percent. Examples of webs containing staple fiber are disclosed in U.S. Pat. No. 4,118,531 (Hauser).

Sorbent particulate material such as activated carbon or alumina may also be included in the web. Such particles may be present in amounts up to about 80 volume percent of the contents of the web. Examples of particle-loaded webs are described, for example, in U.S. Pat. No. 3,971,373 (Braun), U.S. Pat. No. 4,100,324 (Anderson) and U.S. Pat. No. 4,429,001 (Kolpin et al.).

The electret filter media prepared according to the present disclosure generally have a basis weight in the range of about 10 to 500 g/m², and in some embodiments, about 10 to 100 g/m². In making melt-blown microfiber webs, the basis weight can be controlled, for example, by changing either the collector speed or the die throughput. The thickness of the filter media is typically about 0.25 to 20 millimeters, and in some embodiments, about 0.5 to 2 millimeters. The electret filter media and the resin from which it is produced should not be subjected to any unnecessary treatment which might increase its electrical conductivity, e.g., exposure to ionizing radiation, gamma rays, ultraviolet irradiation, pyrolysis, oxidation, etc.

The electret web may be charged as it is formed or the web may be charged after the web is formed. In electret filter media, the media is generally charged after the web is formed. In general, any standard charging method known in the art may be used. For example, charging may be carried out in a variety of ways, including DC corona discharge charging and hydrocharging. A combination of these methods may also be used.

Examples of suitable DC corona discharge processes are described in U.S. Pat. Re. No. 30,782 (van Turnhout), U.S. Pat. Re. No. 31,285 (van Turnhout), U.S. Pat. Re. No. 32,171 (van Turnhout), U.S. Pat. No. 4,215,682 (Davis et al.), U.S. Pat. No. 4,375,718 (Wadsworth et al.), U.S. Pat. No. 5,401,446 (Wadsworth et al.), U.S. Pat. No. 4,588,537 (Klaase et al.), and U.S. Pat. No. 4,592,815 (Nakao).

Hydrocharging of the web is carried out by impinging jets of water or a stream of water droplets onto the web at a pressure sufficient to provide the web with filtration enhancing electret charge. The pressure necessary to achieve optimum results varies depending on the type of sprayer used, the type of polymer from which the web is formed, the type and concentration of additives to the polymer, the thickness and density of the web and whether pretreatment, such as DC corona surface treatment, was carried out prior to hydrocharging. Generally, pressures in the range of about 10 to 500 psi (69 to 3450 kPa) are suitable. Distilled or deionized water is generally preferable to tap water for hydrocharging.

The jets of water or stream of water droplets can be provided by any suitable spray means. An apparatus useful for hydraulically entangling fibers is generally useful in the method of the present disclosure, although operation is carried out at lower pressures in hydrocharging than generally used in hydroentangling. Hydrocharging is understood to include the method described in U.S. Pat. No. 5,496,507 (Angadjivand) and other various derivative methods for imparting an electret charge using the fluid wetting and dewetting process as described in, for example, Japanese Patent Application Number JP 2002161467 (Horiguchi), Japanese Patent Application Number JP 2002173866 (Takeda), Japanese Patent Application Number JP 2002115177 (Takeda), Japanese Patent Application Number JP 2002339232 (Takeda), Japanese Patent Application Number JP 2002161471 (Takeda), Japanese Pat. No. 3,780,916 (Takeda), Japanese Patent Application Number JP 2002115178 (Takeda), Japanese Patent Application Number JP 2003013359 (Horiguchi), U.S. Pat. No. 6,969,484 (Horiguchi), U.S. Pat. No. 6,454,986 (Eitzman), Japanese Patent Application Number JP 2004060110 (Masumori), Japanese Patent Application Number JP 2005131485 (Kodama), and Japanese Patent Application Number JP 2005131484 (Kodama).

In practical use, there may be considerable time lapse between the time the electret filter webs are charged and when they are used. This time encompasses the time required for shipping, storage, etc and may involve a variety of temperature conditions. It is desirable that charge imparted to the web be retained.

To model these considerations, a variety of filtration testing and accelerated aging testing protocols have been developed. These tests include measurement of the aerosol penetration of the filter web using a standard challenge aerosol such as dioctylphthalate (DOP), which is usually presented as percent of aerosol penetration through the filter web (% Pen) and measurement of the pressure drop across the filter web ($\Delta P$). From these two measurements, a quantity known as the quality factor (QF) may be calculated by the following formula:

$$QF=-\ln(\%Pen/100)/\Delta P,$$

where ln stands for the natural logarithm. A higher QF value indicates better filtration performance and decreased QF values effectively correlate with decreased filtration performance. The quality factor of the as generated webs without exposure to other environments is typically designated as "$Q_0$" the Initial Quality Factor. Details for measuring these values are presented in the Examples section.

In order to determine the stability of the filtration performance, accelerated aging can be tested by comparing the initial quality factor of charged BMF webs with its quality factor after storage at different temperatures for different periods of time.

In one test, the webs are stored for 72 hours at 71° C. in air. This quality factor after aging at this condition is typically designated as "$Q_3$". The performance retention is calculated by the following equation:

$$\%\text{Retention}(Q3)=Q3(\text{after aging for 72 hours at 71}°\text{C.})/Q_0(\text{initial})\times100\%.$$

In a more severe accelerated aging test, the webs are stored for 9 hours at 100° C. in air. This quality factor after aging at this condition is typically designated as "$Q_9$". The performance retention is calculated by the following equation:

%Retention($Q_9$)=$Q_9$(after aging for 9 hours at 100° C.)/$Q_0$(initial)×100%.

Typically, the filtration media of this disclosure have measured QF values of 0.3 or greater at a face velocity of 6.9 centimeters per second. In some embodiments the performance retention ($Q_3$) is 90% or greater. In other embodiments the performance retention ($Q_3$) is 91%, 93%, 95% or greater, or even 100%. In some embodiments the performance retention ($Q_9$) is 90% or greater. In other embodiments the performance retention ($Q_9$) is 91%, 93%, 95% or greater, or even 100%.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

DOP aerosol is nominally a monodisperse 0.3 micrometer mass median diameter having an upstream concentration of 100 mg/m$^3$. The aerosol was forced through a sample of filter media at a calibrated flow rate of 42.5 liters/minute (face velocity of 6.9 cm/s) with the aerosol ionizer turned off. The total testing time was 23 seconds (rise time of 15 seconds, sample time of 4 seconds, and purge time of 4 seconds). The concentration of DOP aerosol was measured by light scattering both upstream and downstream of the filter media using calibrated photometers. The DOP % Pen is defined as: % Pen=100×(DOP concentration downstream/DOP concentration upstream). For each material, 6 separate measurements were made at different locations on the BMF web and the results were averaged.

The % Pen and ΔP were used to calculate a QF by the following formula:

$$QF = -\ln(\%Pen/100)/\Delta P,$$

where ln stands for the natural logarithm. A higher QF value indicates better filtration performance and decreased QF values effectively correlate with decreased filtration performance. The quality factor of the as generated webs without exposure to other environments is typically designated as "$Q_0$" the Initial Quality Factor.

Table of Abbreviations

| Abbreviation or Trade Designation | Description |
| --- | --- |
| Charge Additive-1 | 2,4,6-trianilino-p-(carbo-2'-ethylhexyl-1'-oxy)-1,3,5-triazine, shown in Formula III above, commercially available as "UVINUL T-150" from BASF, Ludwigshafen, Germany. |
| Charge Additive-2 | 4,4'[[6-[[4-[[(1,1-dimethylethyl)amino]carbonyl]phenyl]amino]-1,3,5-triazine-2,4-diyl]diimino]bis-benzoic acid bis(2-ethylhexyl) ester, shown in Formula IV above, commercially available as "UVASORB HEB" from 3V Bergamo, Italy. |
| Charge Additive-3 | 2,4,6-trianilino(p-carbo-tetradecyl-oxy)-1,3,5-triazine prepared as described in the Synthesis Section below. |
| Charge Additive-4 | 2,4,6-trianilino(p-carbo-octadecyl-oxy)-1,3,5-triazine prepared as described in the Synthesis Section below. |
| Charge Additive-5 | N,N',N''-tris(4-tetradecyl-phenyl)-1,3,5-triazine-2,4,6-triamine prepared as described in the Synthesis Section below. |
| Charge Additive-6 | N,N',N''-tris(4-octadecylphenyl)-1,3,5-triazine-2,4,6-triamine prepared as described in the Synthesis Section below. |
| Charge Additive-7 | N,N',N''-trioctadecyl-1,3,5-triazine-2,4,6-triamine prepared as described in the Synthesis Section below. |
| Charge Additive-8 | Poly[[6-[(1,1,3,3-tetramethylbutyl)amino]-1,3,5-triazine-2,4-diyl]][(2,2,6,6-tetramethyl-4-piperidinyl)imino]-1,6-hexanediyl](2,2,6,6-tetramethyl-4-piperidinyl)imino]]) commercially available as "CHIMASSORB 944" from Ciba Specialty Chemicals, Basel, Switzerland. |
| PP-1 | Polypropylene resin grade 1, ESCORENE PP 3746G, commercially available from Exxon-Mobil Corporation, Irving, TX. |
| PP-2 | Polypropylene resin grade 2, TOTAL PP3860, commercially available from Total Petrochemicals USA Inc., Houston, TX. |
| PP-3 | Polypropylene resin grade 3, TOTAL PP3960, commercially available from Total Petrochemicals USA Inc., Houston, TX. |

Test Methods
Filtration Testing

The samples were tested for % DOP aerosol penetration (% Pen) and pressure drop (ΔP), and the quality factor (QF) was calculated. The filtration performance (% Pen and QF) of the nonwoven microfiber webs were evaluated using an Automated Filter Tester AFT Model 8127 (available from TSI, Inc., St. Paul, Minn.) using dioctylphthalate (DOP) as the challenge aerosol and a MKS pressure transducer that measured pressure drop (ΔP (mm of H$_2$O)) across the filter. The Accelerated Aging Performance In order to determine the stability of the filtration performance, accelerated aging was tested by comparing the initial quality factor of charged BMF webs with its quality factor after storage at different temperatures for different periods of time.

In one test, the webs are stored for 72 hours at 71° C. in air. This quality factor after aging at this condition is typically designated as "$Q_3$". The performance retention is calculated by the following equation:

%Retention($Q_3$)=$Q_3$(after aging for 72 hours at 71° C.)/$Q_0$(initial)×100%

In a more severe accelerated aging test, the webs are stored for 9 hours at 100° C. in air. This quality factor after aging at this condition is typically designated as "$Q_9$". The performance retention is calculated by the following equation %Retention($Q_9$)=$Q_9$(after aging for 9 hours at 100° C.)/$Q_0$(initial)×100%

SYNTHESIS EXAMPLES

Synthesis Example 1

Preparation of Charge Additive 3

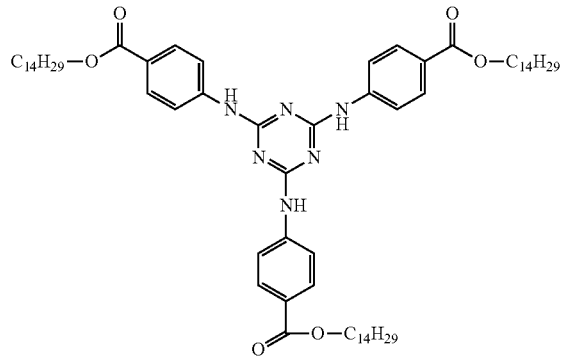

Under a nitrogen atmosphere, a mixture of 1-tetradecanol (96.3 grams, 449 mmol), pyridine (40 milliliters), and dichloromethane (1000 milliliters) was heated to 30° C. 4-Nitrobenzoyl chloride (100 grams, 539 mmol) was added in portions over a twenty minute period. The reaction mixture was heated to reflux for sixteen hours. The reaction mixture was washed with water (2×500 milliliters). The organic layer was concentrated under reduced pressure to a yellow solid. 1000 milliliters of hexane was added and the mixture was heated to reflux. The mixture was cooled and filtered. The filtrate was concentrated to yield a yellow solid. The yellow solid was recrystallized twice from ethanol to obtain 77.0 grams of tetradecyl 4-nitrobenzoate as yellow crystals.

Under a nitrogen purge, 10% platinum on carbon (2.5 grams) was added to a mixture of tetradecyl 4-nitrobenzoate (25 grams, 69 mmol) and ethyl acetate (250 milliliters) in a Parr vessel. The vessel was placed under hydrogen pressure (49 psi, 3.3×10$^5$ Pa) for sixteen hours. Dichloromethane was added and the reaction mixture was filtered through a layer of CELITE filter aid. The filtrate was concentrated under reduced pressure to a tan solid. The solid was recrystallized from ethanol to obtain 15 grams of tetradecyl 4-aminobenzoate as light tan needles.

Under a nitrogen atmosphere, a mixture of tetradecyl 4-aminobenzoate (45.6 grams, 137 mmol) and cyanuric chloride (8.40 grams, 45.6 mmol) in xylene (460 milliliters) was heated to reflux for twenty-four hours. The reaction mixture was cooled to 90° C. and washed with saturated aqueous sodium bicarbonate (2×500 milliliters), followed by water (3×500 milliliters). A white precipitate formed as the xylene cooled overnight. The white precipitate was isolated by filtration and washed with excess xylene. The solid was recrystallized twice from 34:66 dichloromethane:methanol (750 milliliters) and once from xylene (300 milliliters) to provide 27.6 grams of 2,4,6-trianilino(p-carbo-tetradecyl-oxy)-1,3,5-triazine as a white solid.

Compositional Analysis: Calculated for $C_{66}H_{102}N_6O_6$: % C, 73.70; % H, 9.56; % N, 7.81. Found: % C, 73.44; % H, 9.37; % N, 7.62.

Synthesis Example 2

Preparation of Charge Additive 4

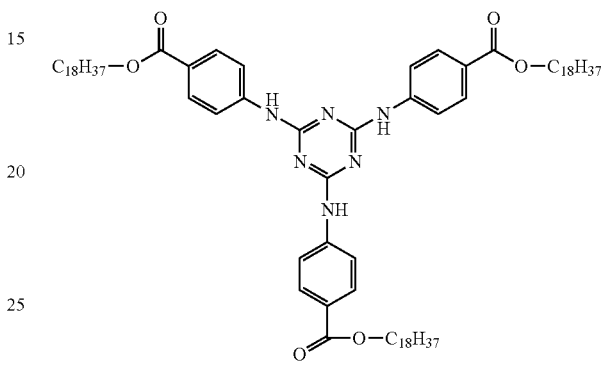

Under a nitrogen atmosphere, a mixture of 1-octadecanol (36 grams, 210 mmol), pyridine (20 milliliters), and dichloromethane (500 milliliters) was heated to reflux. The alcohol dissolved and the solution was allowed to cool 5° C. 4-Nitrobenzoyl chloride (39.0 grams, 210 mmol) was added in portions over a twenty minute period. The reaction mixture was heated to reflux for sixteen hours. The reaction mixture was washed with 250 milliliters of water. The aqueous layer was washed with 250 milliliters of dichloromethane. The organic layers were combined and concentrated under reduced pressure to a light tan solid. Added 500 milliliters of hexane and heated to reflux. A white precipitate formed as the solution was cooled to room temperature. Filtered off the white precipitate and concentrated the filtrate to a light tan solid. The solid was recrystallized from ethanol (500 milliliters) to obtain 46 grams of octadecyl 4-nitrobenzoate as a white solid.

Under a nitrogen purge, 10% platinum on carbon (2.0 grams) was added to a mixture of octadecyl 4-nitrobenzoate (23 grams, 55 mmol) and ethyl acetate (230 milliliters) in a Parr vessel. The vessel was placed under hydrogen pressure (49 psi, 3.3×10$^5$ Pa) for sixteen hours. Added chloroform and filtered the reaction mixture through a layer of CELITE filter aid. The filtrate was concentrated under reduced pressure to light tan solid. The solid was recrystallized from ethanol to obtain 18 grams of octadecyl 4-aminobenzoate as a white solid.

Under a nitrogen atmosphere, a mixture of octadecyl 4-aminobenzoate (40.1 grams, 103 mmol) and cyanuric chloride (6.30 grams, 34.2 mmol) in xylene (350 milliliters) was heated to reflux for twenty-four hours. The reaction mixture was cooled to 90° C. and stirred with 175 milliliters of saturated aqueous sodium bicarbonate for two hours. A white precipitate formed as the mixture cooled overnight. The white precipitate was isolated by filtration and washed with excess xylene and water. The solid was recrystallized from 90:10 chloroform:methanol (500 milliliters) to provide 38.2 grams of 2,4,6-trianilino(p-carbo-octadecyl-oxy)-1,3,5-triazine as a white solid.

Compositional Analysis: Calculated for $C_{78}H_{126}N_6O_6$: % C, 75.32; % H, 10.21; % N, 6.76. Found: % C, 75.27; % H, 10.16; % N, 6.72.

Synthesis Example 3

Preparation of Charge Additive 5

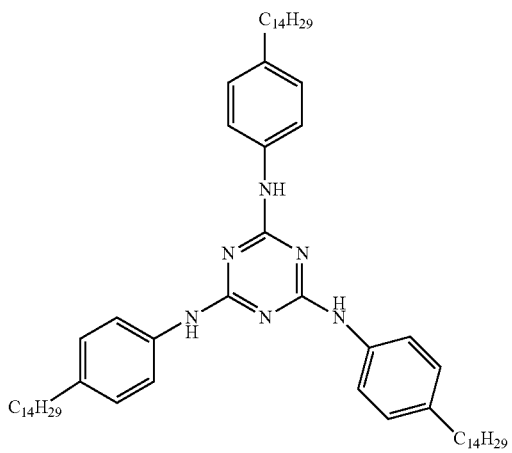

Under a nitrogen atmosphere, a mixture of 4-tetradecylanaline (50.0 grams, 173 mmol) and cyanuric chloride (10.6 grams, 57.6 mmol) in xylene (500 milliliters) was heated to reflux for twenty-four hours. The reaction mixture was cooled to 90° C. and washed with saturated aqueous sodium bicarbonate (2×500 milliliters) followed by water (3×500 milliliters). A white precipitate formed as the xylene cooled overnight. The white precipitate was isolated by filtration and washed with excess xylene. The solid was recrystallized twice from 34:66 chloroform:methanol (750 milliliters) and once from xylene (300 milliliters) to provide 30.0 grams of N,N',N"-tris(4-tetradecyl-phenyl)-1,3,5-triazine-2,4,6-triamine as a white solid.

Compositional Analysis: Calculated for $C_{63}H_{102}N_6$: % C, 80.20; % H, 10.90; % N, 8.91. Found: % C, 80.16; % H, 11.05; % N, 8.92.

Synthesis Example 4

Preparation of Charge Additive 6

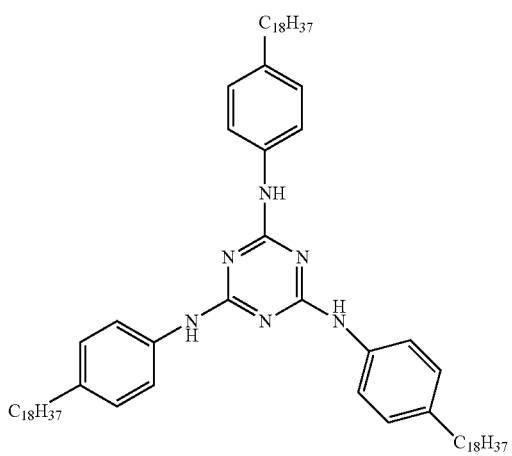

Under a nitrogen atmosphere, a mixture of 4-octadecylanaline (50 grams, 145 mmol) and cyanuric chloride (8.9 grams, 48 mmol) in xylene (500 milliliters) was heated to reflux for twenty-four hours. The reaction mixture was cooled to 90° C. and washed with saturated aqueous sodium bicarbonate (2×500 milliliters) followed by water (2×500 milliliters). A white precipitate formed as the xylene cooled overnight. The white precipitate was isolated by filtration and washed with excess xylene. The solid was recrystallized twice from 90:10 chloroform:methanol (500 milliliters) and once from xylene (500 milliliters) to provide 45 grams of N,N',N"-tris(4-octadecylphenyl)-1,3,5-triazine-2,4,6-triamine as a white solid.

Compositional Analysis Calculated for $C_{75}H_{126}N_6$: % C, 81.02; % H, 11.42; % N, 7.56. Found: % C, 81.05; % H, 11.38; % N, 7.60.

Synthesis Example 5

Preparation of Charge Additive 7

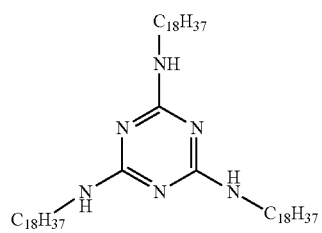

Under a nitrogen atmosphere, a mixture of octadecylamine (389 grams, 1.44 mol), di(propylene glycol) dimethyl ether (1.50 liters), sodium acetate (134 grams, 1.63 mol), and cyanuric chloride (88.4 grams, 0.479 mol) was stirred for thirty minutes and then heated to 85° C. for two hours. The reaction mixture was heated to 155° C. at which temperature acetic acid was allowed to reflux out of the reaction mixture. The reaction mixture was heated to 170° C. for sixteen hours. 2-Propanol (1.60 liters) was added to the reaction mixture when it had cooled to 80° C. The precipitate was filtered at room temperature and washed with excess 2-propanol. The solid was stirred in refluxing water (2.00 liters) for two hours, filtered, and washed with excess water. The solid was stirred in refluxing 2-propanol (2.00 liters), filtered, and washed with excess 2-propanol to yield 377 grams of N,N',N"-trioctadecyl-1,3,5-triazine-2,4,6-triamine as a white solid.

Thermal Stability Analysis:

The thermal stability of each charging additive was measured with a Thermogravimetric Analyzer (TGA) Model 2950 available from TA Instruments, New Castle, Del. Approximately 5-10 milligrams of material was placed in the TGA and heated from room temperature to 500° C. at a rate of 10° C./min under an air environment while the weight loss due to thermal decomposition was measured. Table 1 lists the temperature at which 2% weight loss was detected.

TABLE 1

| Charging Additive | Temperature at 2% weight loss (° C.) |
|---|---|
| 1 | 321 |
| 2 | 340 |
| 3 | 285 |
| 4 | 274 |
| 5 | 316 |
| 6 | 290 |

TABLE 1-continued

| Charging Additive | Temperature at 2% weight loss (° C.) |
|---|---|
| 7 | 216 |
| 8 | 264 |

Examples 1-31 and Comparative Examples C1-C25

For each of the Examples and Comparative Examples, the procedures described below were followed. The data for these Examples are presented in Tables 2 and 3.

Sample Preparation

Step A—Preparation of Microfiber Webs

For each Example, one of the charging additives described above (either Additive 1, 2, 3 or 4) was selected and dry blended with one of the 3 grades of polypropylene at the concentration shown in Table 2, and the blend was extruded as described in Van A. Wente, "Superfine Thermoplastic Fibers," Industrial Engineering Chemistry, vol. 48, pp. 1342-1346. The extrusion temperature ranged from about 250° C.-300° C. and the extruder was a BRABENDER conical twin-screw extruder (commercially available from Brabender Instruments, Inc.) operating at a rate of about 2.5 to 3 kg/hr (5-7 lb/hr). The die was 25.4 cm (10 in) wide with 10 holes per centimeter (25 holes per inch). Melt blown microfiber (BMF) webs were formed having basis weights of about 50-60 g/m$^2$, effective fiber diameters of about 6.5-9.5 micrometers and a thicknesses of about 0.75-2 millimeters.

Likewise, for each Comparative Example, a BMF web was prepared from the same grade of polypropylene as the corresponding Examples web, but either no charge additive was added or one of the charging additives 5, 6, 7, or 8 was used. Table 2 summarizes the specific web characteristics for each of the comparative examples.

Step B—Electret Preparation:

Each of the BMF webs prepared in Step A above was charged by one of three electret charging methods: hydrocharging, corona charging, or corona pre-treatment and hydrocharging. Table 2 summarizes the specific charging method applied to each of the samples.

Charging Method 1—Hydrocharging:

A fine spray of high purity water having a conductivity of less than 5 microS/cm was continuously generated from a nozzle operating at a pressure of 896 kiloPascals (130 psig) and a flow rate of approximately 1.4 liters/minute. The selected BMF webs prepared in Step A were conveyed by a porous belt through the water spray at a speed of approximately 10 centimeters/second while a vacuum simultaneously drew the water through the web from below. Each BMF web was run through the hydrocharger twice (sequentially once on each side) and then allowed to dry completely overnight prior to filter testing.

Charging Method 2—Corona Charging:

The selected BMF webs prepared in Step A above were charged by DC corona discharge. The corona charging was accomplished by passing the web on a grounded surface under a corona brush source with a corona current of about 0.01 milliamp per centimeter of discharge source length at a rate of about 3 centimeters per second. The corona source was about 3.5 centimeters above the grounded surface on which the web was carried. The corona source was driven by a positive DC voltage.

Charging Method 3—Corona Pre-treatment and Hydrocharging:

The selected BMF webs prepared in Step A above were pretreated by DC corona discharge as described in Charging Method 2 and then charged by hydrocharging as described in Charging Method 1.

Filtration Testing Procedure

Initial Filtration Performance:

Each of the charged samples prepared in Step B above was cut into two 1 meter sections. One section was tested in its initial state for % DOP aerosol penetration (% Pen) and pressure drop ($\Delta P$), and the quality factor (QF) was calculated as described in the Test Methods given above. These results are reported in Table 3 below as Initial % Pen, Initial $\Delta P$ and Initial QF.

Accelerated Aging Filtration Performance:

In order to determine the stability of the filtration performance, accelerated aging testing was done to determine the % Charge Retention as described in the Test Method above. The other 1 meter section of each sample prepared in Step B was subjected to one of two accelerated thermal aging regimens as reported in Table 3.

Thermal Aging Regimen 1: Heating for 3 days at 71° C.
Thermal Aging Regimen 2: Heating for 9 hours at 100° C.

After thermal aging each sample section was tested for % DOP aerosol penetration (% Pen) and pressure drop ($\Delta P$), and the quality factor (QF) was calculated as described in the Test Methods given above. These results are reported in Table 3 as Aged % Pen, Aged $\Delta P$ and Aged QF. Finally, for each sample the % Retention was calculated by comparing the Initial and Aged QF values as described in the Test Methods and is reported in Table 3.

TABLE 2

| Example | Charging Additive | Charging Method | Resin Grade | Additive Concn. (wt %) | Eff. Fiber Diam. (μm) | Solidity (%) | Basis Weight (g/m$^2$) | Thickness (mm) |
|---|---|---|---|---|---|---|---|---|
| 1 | 2 | 1 | PP-3 | 0.25 | 7.1 | 4.7 | 58 | 1.47 |
| 2 | 2 | 1 | PP-3 | 0.5 | 8.2 | 5.1 | 57 | 1.45 |
| 3 | 2 | 1 | PP-3 | 0.75 | 8 | 5.7 | 57 | 1.45 |
| 4 | 2 | 1 | PP-3 | 1 | 8 | 5.7 | 55 | 1.40 |
| C1 | None | 1 | PP-3 | 0 | 7.9 | 4.9 | 55 | 1.40 |
| 5 | 2 | 3 | PP-3 | 0.25 | 7.1 | 4.7 | 58 | 1.47 |
| 6 | 2 | 3 | PP-3 | 0.5 | 8.2 | 5.1 | 57 | 1.45 |
| 7 | 2 | 3 | PP-3 | 0.75 | 8 | 5.7 | 57 | 1.45 |
| 8 | 2 | 3 | PP-3 | 1 | 8 | 5.7 | 55 | 1.40 |
| C2 | None | 3 | PP-3 | 0 | 7.9 | 4.9 | 55 | 1.40 |
| 9 | 1 | 2 | PP-1 | 0.25 | 8.6 | 5.1 | 60 | 1.52 |
| 10 | 1 | 2 | PP-1 | 0.5 | 8.1 | 5 | 62 | 1.57 |
| 11 | 1 | 2 | PP-1 | 1 | 8.1 | 5.3 | 61 | 1.55 |
| 12 | 1 | 2 | PP-1 | 1.5 | 8.3 | 5.4 | 61 | 1.55 |

TABLE 2-continued

| Example | Charging Additive | Charging Method | Resin Grade | Additive Concn. (wt %) | Eff. Fiber Diam. (μm) | Solidity (%) | Basis Weight (g/m$^2$) | Thickness (mm) |
|---|---|---|---|---|---|---|---|---|
| C3 | None | 2 | PP-1 | 0 | 8.2 | 4.8 | 58 | 1.47 |
| 13 | 1 | 1 | PP-1 | 0.1 | 7.6 | 5.1 | 64 | 1.63 |
| 14 | 1 | 1 | PP-1 | 0.25 | 8.2 | 5.4 | 64 | 1.63 |
| 15 | 1 | 1 | PP-1 | 0.5 | 8.3 | 5.4 | 57 | 1.45 |
| 16 | 1 | 1 | PP-1 | 0.75 | 8.1 | 5.6 | 62 | 1.57 |
| C4 | None | 1 | PP-1 | 0 | 8 | 5.4 | 60 | 1.52 |
| 17 | 2 | 3 | PP-2 | 1 | 8.4 | 6.1 | 54 | 1.37 |
| 18 | 1 | 3 | PP-2 | 1 | 7 | 6.1 | 56 | 1.42 |
| C5 | None | 3 | PP-2 | 0 | 7.7 | 6.4 | 56 | 1.42 |
| 19 | 4 | 3 | PP-1 | 1 | 7.1 | 3.9 | 60 | 1.52 |
| 20 | 2 | 3 | PP-1 | 1 | 6.7 | 4.6 | 59 | 1.50 |
| C6 | 7 | 3 | PP-1 | 1 | 8.4 | 5 | 60 | 1.52 |
| C7 | 6 | 3 | PP-1 | 1 | 7.4 | 4.6 | 60 | 1.52 |
| C8 | None | 3 | PP-1 | 0 | 8.1 | 4.7 | 59 | 1.50 |
| 21 | 4 | 1 | PP-1 | 1 | 7.1 | 3.9 | 60 | 1.52 |
| 22 | 2 | 1 | PP-1 | 1 | 6.7 | 4.6 | 59 | 1.50 |
| C9 | None | 1 | PP-1 | 0 | 8.1 | 4.7 | 59 | 1.50 |
| C10 | 7 | 1 | PP-1 | 1 | 8.4 | 5 | 60 | 1.52 |
| C11 | 6 | 1 | PP-1 | 1 | 7.4 | 4.6 | 60 | 1.52 |
| 23 | 3 | 1 | PP-3 | 1 | 7.7 | 4.6 | 57 | 1.37 |
| C12 | None | 1 | PP-3 | 1 | 7.6 | 5.7 | 59 | 1.14 |
| C13 | 6 | 1 | PP-3 | 0 | 6.8 | 5 | 54 | 1.19 |
| C14 | 8 | 1 | PP-3 | 1 | 7.6 | 6.1 | 62 | 1.12 |
| C15 | 7 | 1 | PP-3 | 1 | 8.3 | 5.3 | 63 | 1.30 |
| 24 | 3 | 1 | PP-1 | 1 | 8.7 | 4.6 | 57 | 1.40 |
| 25 | 4 | 1 | PP-1 | 1 | 8.3 | 4.7 | 62 | 1.47 |
| C16 | 5 | 1 | PP-1 | 1 | 7.5 | 6 | 53 | 0.97 |
| C17 | 6 | 1 | PP-1 | 1 | 7.4 | 4.6 | 60 | 1.45 |
| C18 | 7 | 1 | PP-1 | 1 | 9.1 | 5.2 | 60 | 1.27 |
| C19 | None | 1 | PP-1 | 0 | 7.6 | 5.3 | 55 | 1.17 |
| 26 | 3 | 3 | PP-1 | 1 | 8.7 | 4.6 | 57 | 1.40 |
| 27 | 4 | 3 | PP-1 | 1 | 8.3 | 4.7 | 62 | 1.47 |
| C20 | 5 | 3 | PP-1 | 1 | 7.5 | 6 | 53 | 0.97 |
| C21 | 6 | 3 | PP-1 | 1 | 8 | 6.2 | 53 | 0.94 |
| C22 | 7 | 3 | PP-1 | 1 | 8.5 | 5.3 | 61 | 1.27 |
| C23 | 8 | 3 | PP-1 | 1 | 8.1 | 5.1 | 59 | 1.30 |
| C24 | None | 3 | PP-1 | 0 | 8.7 | 5.5 | 64 | 1.27 |
| 28 | 2 | 3 | PP-1 | 0.50 | 8.2 | 5.4 | 58 | 1.47 |
| 29 | 2 | 3 | PP-1 | 1 | 8.7 | 5.9 | 55 | 1.40 |
| 30 | 2 | 3 | PP-1 | 1.50 | 9.6 | 6 | 58 | 1.47 |
| 31 | 2 | 3 | PP-1 | 2 | 9.6 | 6 | 55 | 1.40 |
| C25 | None | 3 | PP-1 | 0 | 8.8 | 6.1 | 57 | 1.45 |

TABLE 3

| Example | Initial % Pen | Initial Pressure Drop (mm of H$_2$O) | Initial QF | Aging Condition | Aged % Pen | Aged Pressure Drop (mm of H$_2$O) | Aged QF | Charge Retention (%) |
|---|---|---|---|---|---|---|---|---|
| 1 | 10.32 | 2.37 | 0.96 | 1 | 10.06 | 2.4 | 0.96 | 100% |
| 2 | 6.9 | 2.22 | 1.20 | 1 | 8.84 | 2.09 | 1.16 | 97% |
| 3 | 12.52 | 1.73 | 1.20 | 1 | 13.35 | 1.62 | 1.24 | 103% |
| 4 | 8.55 | 2.07 | 1.19 | 1 | 8.79 | 2 | 1.22 | 103% |
| C1 | 50.5 | 2.13 | 0.32 | 1 | 61.22 | 2.07 | 0.24 | 75% |
| 5 | 3.21 | 2.68 | 1.3 | 1 | 4.49 | 2.47 | 1.27 | 98% |
| 6 | 4.11 | 2.18 | 1.47 | 1 | 4.66 | 2.13 | 1.46 | 99% |

TABLE 3-continued

| Example | Initial % Pen | Initial Pressure Drop (mm of H$_2$O) | Initial QF | Aging Condition | Aged % Pen | Aged Pressure Drop (mm of H$_2$O) | Aged QF | Charge Retention (%) |
|---|---|---|---|---|---|---|---|---|
| 7 | 7.87 | 1.72 | 1.49 | 1 | 8.17 | 1.6 | 1.58 | 106% |
| 8 | 5.12 | 1.95 | 1.54 | 1 | 5.96 | 1.88 | 1.52 | 99% |
| C2 | 22 | 2.22 | 0.7 | 1 | 32.2 | 1.93 | 0.6 | 86% |
| 9 | 25.3 | 1.98 | 0.69 | 1 | 26 | 1.8 | 0.75 | 109% |
| 10 | 18.1 | 1.85 | 0.92 | 1 | 23.3 | 1.72 | 0.85 | 92% |
| 11 | 19.4 | 1.67 | 0.98 | 1 | 21.5 | 1.72 | 0.89 | 91% |
| 12 | 25.4 | 1.62 | 0.85 | 1 | 22.2 | 1.68 | 0.90 | 106% |
| C3 | 31.2 | 1.82 | 0.64 | 1 | 39.1 | 1.95 | 0.48 | 75% |
| 13 | 7.25 | 2.43 | 1.08 | 1 | 8.33 | 2.3 | 1.08 | 100% |
| 14 | 4.44 | 2.57 | 1.21 | 1 | 6.17 | 2.4 | 1.16 | 96% |
| 15 | 2.89 | 2.57 | 1.38 | 1 | 3.69 | 2.48 | 1.33 | 96% |
| 16 | 2.79 | 2.43 | 1.47 | 1 | 3.33 | 2.37 | 1.44 | 98% |
| C4 | 20.32 | 2.35 | 0.68 | 1 | 24.23 | 2.33 | 0.61 | 90% |
| 17 | 6.6 | 2.2 | 1.24 | 1 | 8.4 | 2 | 1.24 | 100% |
| 18 | 4.6 | 2.4 | 1.28 | 1 | 5.0 | 2.3 | 1.30 | 102% |
| C5 | 12.6 | 1.9 | 1.09 | 1 | 23.2 | 2.1 | 0.70 | 64% |
| 19 | 3.69 | 2.5 | 1.32 | 1 | 5.3 | 2.22 | 1.29 | 98% |
| 20 | 2.97 | 2.71 | 1.22 | 1 | 4.31 | 2.61 | 1.23 | 101% |
| C6 | 1.85 | 2.18 | 1.83 | 1 | 6.06 | 1.96 | 1.43 | 78% |
| C7 | 14.14 | 2.77 | 0.71 | 1 | 16.7 | 2.47 | 0.73 | 103% |
| C8 | 15.4 | 2.48 | 0.75 | 1 | 33.8 | 2.1 | 0.52 | 69% |
| 21 | 9.1 | 2.6 | 0.91 | 1 | 10.96 | 2.56 | 0.86 | 95% |
| 22 | 6.93 | 2.85 | 0.94 | 1 | 7.02 | 2.76 | 0.96 | 102% |
| C9 | 51.97 | 2.25 | 0.29 | 1 | 64.1 | 2 | 0.22 | 76% |
| C10 | 1.79 | 2.08 | 1.93 | 1 | 4.75 | 2 | 1.51 | 78% |
| C11 | 23.4 | 2.65 | 0.55 | 1 | 26.58 | 2.4 | 0.54 | 98% |
| 23 | 4.73 | 2.07 | 1.47 | 1 | 4.83 | 2.11 | 1.44 | 97% |
| C12 | 15.88 | 2.52 | 0.73 | 1 | 27.42 | 2.42 | 0.53 | 73% |
| C13 | 7.45 | 3.23 | 0.80 | 1 | 10.4 | 3.38 | 0.67 | 83% |
| C14 | 0.98 | 3.05 | 1.52 | 1 | 2.52 | 2.97 | 1.24 | 82% |
| C15 | 4.01 | 2.05 | 1.57 | 1 | 5.26 | 2.13 | 1.38 | 88% |
| 24 | 8.07 | 1.7 | 1.48 | 1 | 9.08 | 1.67 | 1.44 | 97% |
| 25 | 4.84 | 2.43 | 1.25 | 1 | 7.13 | 2.2 | 1.20 | 96% |
| C16 | 13.02 | 2.34 | 0.87 | 1 | 20.98 | 2.18 | 0.72 | 82% |
| C17 | 4.33 | 2.55 | 1.23 | 1 | 13.28 | 2.52 | 0.80 | 65% |
| C18 | 7.93 | 1.7 | 1.49 | 1 | 11.98 | 1.67 | 1.27 | 85% |
| C19 | 12.12 | 2.48 | 0.85 | 1 | 23.2 | 2.3 | 0.64 | 75% |
| 26 | 9.67 | 1.58 | 1.48 | 1 | 11.1 | 1.48 | 1.49 | 100% |
| 27 | 3.03 | 2.55 | 1.37 | 1 | 4.83 | 2.23 | 1.36 | 99% |
| C20 | 5.83 | 2.53 | 1.12 | 1 | 12.06 | 2.42 | 0.87 | 78% |
| C21 | 4.42 | 2.57 | 1.21 | 1 | 14.52 | 2.1 | 0.92 | 76% |
| C22 | 5.58 | 1.8 | 1.60 | 1 | 9.41 | 1.87 | 1.26 | 79% |
| C23 | 2.12 | 2.37 | 1.63 | 1 | 3.59 | 2.38 | 1.40 | 86% |
| C24 | 17.58 | 2.42 | 0.72 | 1 | 25.8 | 2.35 | 0.58 | 80% |
| 28 | 1.6 | 3.4 | 1.22 | 2 | 3.3 | 3 | 1.14 | 93% |
| 29 | 8.2 | 1.7 | 1.47 | 2 | 10.4 | 1.6 | 1.41 | 96% |
| 30 | 9.2 | 1.7 | 1.40 | 2 | 10.8 | 1.6 | 1.39 | 99% |
| 31 | 12.5 | 1.6 | 1.30 | 2 | 14.5 | 1.4 | 1.38 | 106% |
| C25 | 13.8 | 1.8 | 1.10 | 2 | 24.5 | 1.7 | 0.83 | 75% |

What is claimed is:

1. An electret web comprising:
   a thermoplastic resin; and
   a charge additive comprising an ester-substituted and/or amide-substituted trianilino triazine material, wherein the web comprises a non-woven microfiber web.

2. The electret web of claim 1 wherein the ester-substituted and/or amide-substituted trianilino triazine material comprises the structure (a):

(a)
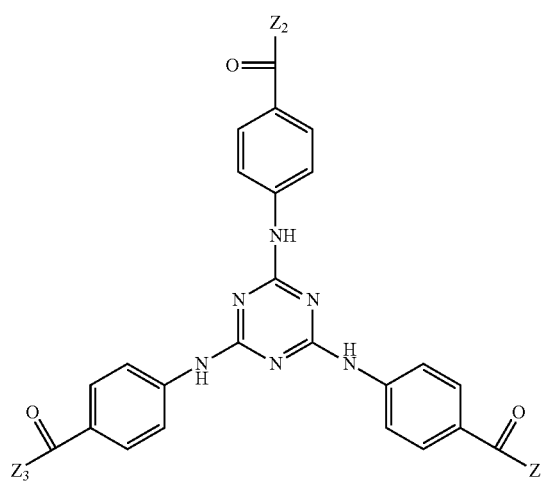

wherein $Z_1$, $Z_2$ and $Z_3$ is each independently —$OR^4$ or —$NR^5R^6$,
where each $R^4$ is independently a linear or branched alkyl group, a substituted alkyl group, a heteroalkyl group, or an aryl group;
each $R^5$ is independently H or a linear or branched alkyl group, a substituted alkyl group, a heteroalkyl group, or an aryl group;
each $R^6$ is independently a linear or branched alkyl group, a substituted alkyl group, a heteroalkyl group, or an aryl group, the structures (b)-(e):

(b)
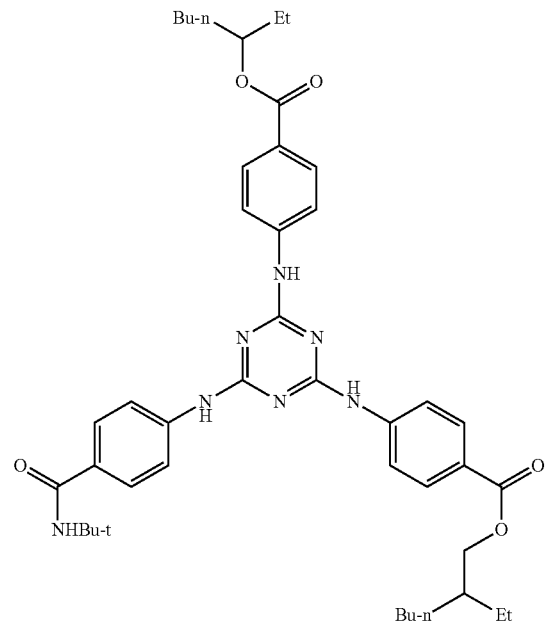

(c)
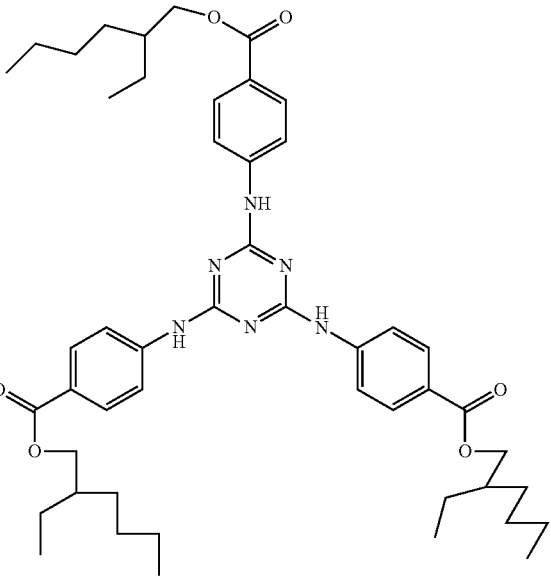

(d)
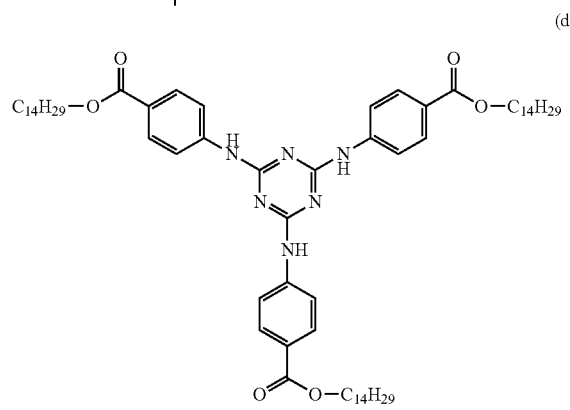

(e)
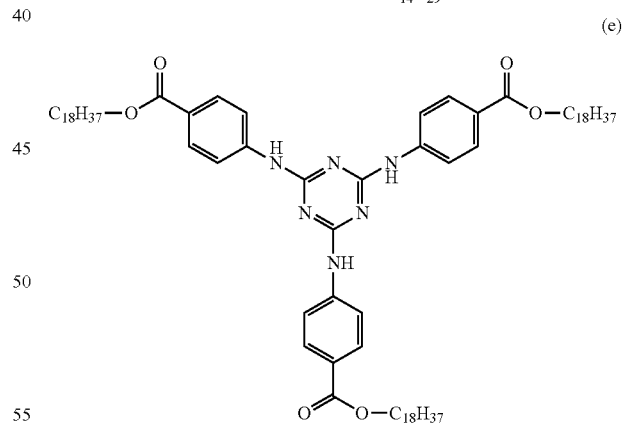

or combinations thereof.

3. The electret web of claim 1 wherein the thermoplastic microfibers comprise:
   polyolefin; polyvinyl chloride; polystyrene; polycarbonate; or polyester;
   polypropylene; poly(4-methyl-1-pentene); copolymers of propylene and 4-methyl-1-pentene; or mixtures thereof.

4. The electret web of claim 1 wherein the ester-substituted and/or amide-substituted trianilino triazine material comprises 0.1-5.0% by weight of the web.

5. An electret filter media comprising:
   a non-woven microfiber web comprising a blend of:
   a thermoplastic resin; and
   a charge additive comprising an ester-substituted and/or amide-substituted trianilino triazine material.

6. The electret filter media of claim 5 wherein the ester-substituted and/or amide-substituted trianilino triazine material comprises the structure (a):

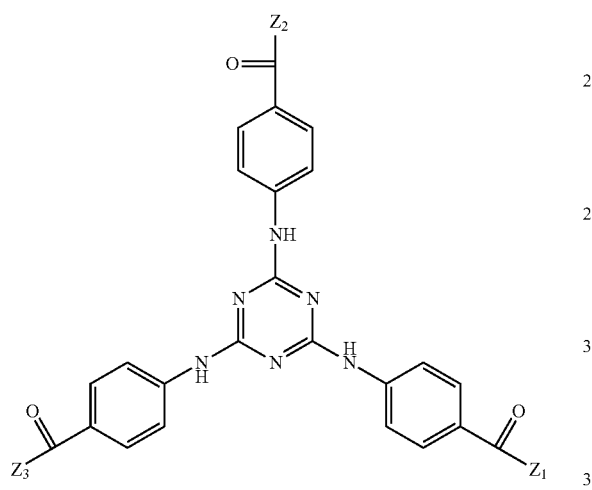

(a)

wherein $Z_1$, $Z_2$ and $Z_3$ is each independently —OR$^4$ or —NR$^5$R$^6$,
where each R$^4$ is independently a linear or branched alkyl group, a substituted alkyl group, a heteroalkyl group, or an aryl group;
each R$^5$ is independently H or a linear or branched alkyl group, a substituted alkyl group, a heteroalkyl group, or an aryl group;
each R$^6$ is independently a linear or branched alkyl group, a substituted alkyl group, a heteroalkyl group, or an aryl group.

7. The electret web of claim 5 wherein each $Z_1$ and $Z_2$ is independently —OR$^4$ where each R$^4$ is independently a linear or branched alkyl group containing from 1 to 20 carbon atoms and $Z_3$ is —OR$^4$ where R$^4$ is a linear or branched alkyl group containing from 1 to 20 carbon atoms or —NR$^5$R$^6$ where R$^5$ is H or a linear or branched alkyl group containing from 1 to 20 carbon atoms and R$^6$ is a linear or branched alkyl group containing from 1 to 20 carbon atoms.

8. The electret filter media of claim 5 wherein the ester-substituted and/or amide-substituted trianilino triazine material comprises the structures (b)-(e):

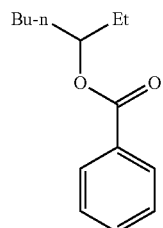

(b)

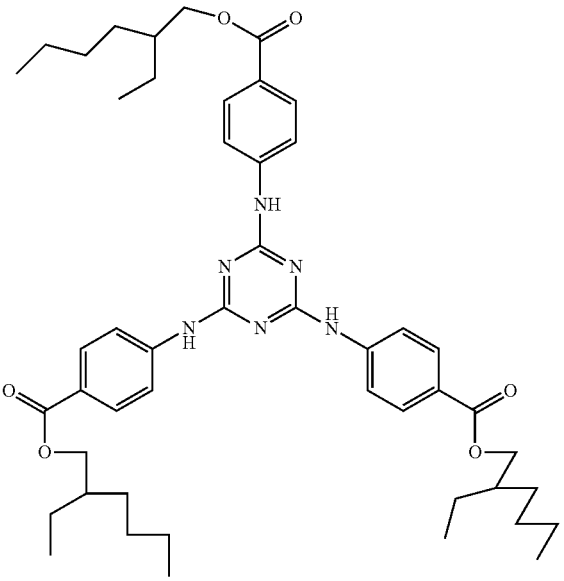

(c)

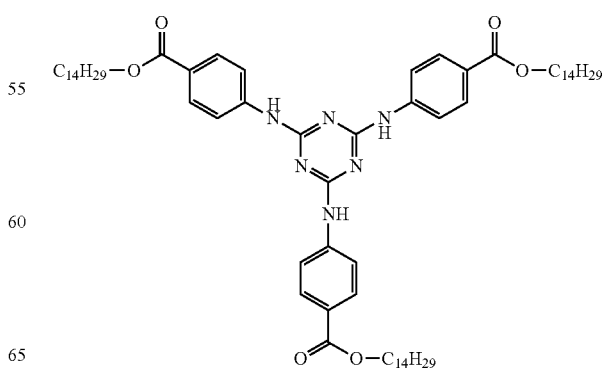

(d)

-continued (e)

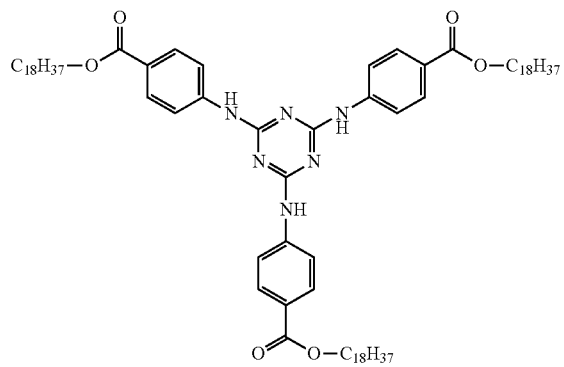

or combinations thereof.

9. The electret filter media of claim 5 wherein the thermoplastic microfibers comprise:
polyolefin; polyvinyl chloride; polystyrene; polycarbonate; or polyester.

10. The electret filter media of claim 5 wherein the thermoplastic microfibers comprise:
polypropylene; poly(4-methyl-1-pentene); copolymers of propylene and 4-methyl-1-pentene; or mixtures thereof.

11. The electret filter media of claim 5 wherein the ester-substituted and/or amide-substituted trianilino triazine material comprises 0.1-5.0% by weight of the web.

12. The electret filter media of claim 5 wherein the web contains a charge, wherein the charge is imparted through hydrocharging, DC corona treatment or a combination thereof.

13. The electret filter media of claim 12 wherein the web has sufficient electrostatic charge to exhibit filtration performance as measured by QF of 0.3 or greater at a face velocity of 6.9 centimeters per second.

14. The electret filter media of claim 13 wherein the web retains at least 91% filtration performance as measured by QF after aging for 72 hours at 71° C.

15. The electret filter media of claim 5 wherein the filter media comprises:
a respirator filter, a room ventilation system filter, a vehicle ventilation system filter, an air conditioner filter, a furnace filter, a room air purifier filter, a vacuum cleaner filter, or a computer disk drive filter.

16. A method of preparing an electret web comprising:
providing a thermoplastic material;
providing a hot melt processable charge additive comprising an ester-substituted and/or amide-substituted trianilino triazine material;
hot melt mixing the thermoplastic material and the charge additive;
melt blowing the mixed thermoplastic material and charge additive to form a microfiber web; and
electrostatically charging the web.

17. The method of claim 16 wherein the ester-substituted and/or amide-substituted trianilino triazine material is represented by structure (a):

(a)

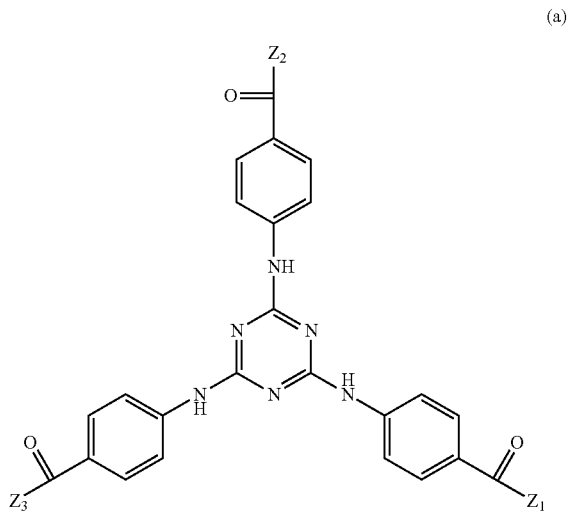

wherein $Z_1$, $Z_2$ and $Z_3$ is each independently —OR$^4$ or —NR$^5$R$^6$,
where each R$^4$ is independently a linear or branched alkyl group, a substituted alkyl group, a heteroalkyl group, or an aryl group;
each R$^5$ is independently H or a linear or branched alkyl group, a substituted alkyl group, a heteroalkyl group, or an aryl group;
each R$^6$ is independently a linear or branched alkyl group, a substituted alkyl group, a heteroalkyl group, or an aryl group.

18. The method of claim 16 wherein the thermoplastic material comprises:
polypropylene; poly(4-methyl-1-pentene); copolymers of propylene and 4-methyl-1-pentene; and mixtures thereof.

19. The method of claim 16 wherein the hot melt processable charge additive comprises 0.1-5.0% by weight of the formed microfiber web.

20. The method of claim 16 wherein charging comprises DC corona discharge treatment, hydrocharging or a combination thereof.

* * * * *

UNITED STATES PATENT AND TRADEMARK OFFICE
CERTIFICATE OF CORRECTION

PATENT NO. : 8,529,671 B2
APPLICATION NO. : 12/746112
DATED : September 10, 2013
INVENTOR(S) : Sebastian et al.

It is certified that error appears in the above-identified patent and that said Letters Patent is hereby corrected as shown below:

On the title page item [73]
Line 1, Delete "Comany," and insert -- Company, --, therefor.

Column 2 (title page 2-3 – item [56] Other Publications)
Line 4, Delete "Mechanaical" and insert -- Mechanical --, therefor.
Line 15-16, Delete "Nonbounded Interactioins," and insert -- Nonbonded Interactions, --, therefor.

In the specification

Column 6
Line 42, Delete "Farrel" and insert -- Farrell --, therefor.

Column 7
Line 3, Delete "air line" and insert -- airline --, therefor.

Column 8
Line 66, Delete "%Retetion(Q3)=Q3" and insert -- %Retetion($Q_3$)=$Q_3$ --, therefor.

Column 9
Line 23, Delete "hexanediyl]" and insert -- hexanediyl[ --, therefor.

Column 11
Line 9, Delete "equation" and insert -- equation: --, therefor.

Column 14
Line 11, Delete "Analysis" and insert -- Analysis: --, therefor.

In the claim

Column 23
Line 55, Claim 7, delete "electret web" and insert -- electret filter media --, therefor.

Signed and Sealed this
Twenty-first Day of April, 2015

Michelle K. Lee
*Director of the United States Patent and Trademark Office*